(12) United States Patent
Nadon et al.

(10) Patent No.: US 6,567,750 B1
(45) Date of Patent: May 20, 2003

(54) PROCESS FOR EVALUATING CHEMICAL AND BIOLOGICAL ASSAYS

(75) Inventors: Robert Nadon, St. Catharines (CA); Peter Ramm, St. Catharines (CA)

(73) Assignee: Imaging Research, Inc., St. Catharines (CA)

( * ) Notice: Subject to any disclaimer, the term of this patent is extended or adjusted under 35 U.S.C. 154(b) by 0 days.

(21) Appl. No.: 09/693,623

(22) Filed: Oct. 20, 2000

Related U.S. Application Data

(63) Continuation of application No. PCT/IB99/00734, filed on Apr. 22, 1999.
(60) Provisional application No. 60/082,692, filed on Apr. 22, 1998.

(51) Int. Cl.[7] .............................. G06F 19/00; C12Q 1/68
(52) U.S. Cl. .............................................. 702/19; 435/6
(58) Field of Search .................................. 702/19; 435/6

*Primary Examiner*—John S. Brusca
(74) *Attorney, Agent, or Firm*—Darby & Darby

(57) ABSTRACT

An analytical process is disclosed, for discriminating data acquired from samples with overlapping distributions, and for improving and assessing the statistical validity of hybridization signal in arrays of assays. The process includes method of convolving data into two or more discrete probability density functions representing signal and nonsignal, discrete fluors, or other convolved independent variables. The system uses the probability density functions to assign hybridization signals, objectively, to one of the modeled distributions. Subsequent processes assess variability inherent to the arrays, and use this assessed variation to establish reliability scores and confidence limits for complete hybridization arrays, and for discrete hybridization assays within arrays.

10 Claims, 8 Drawing Sheets

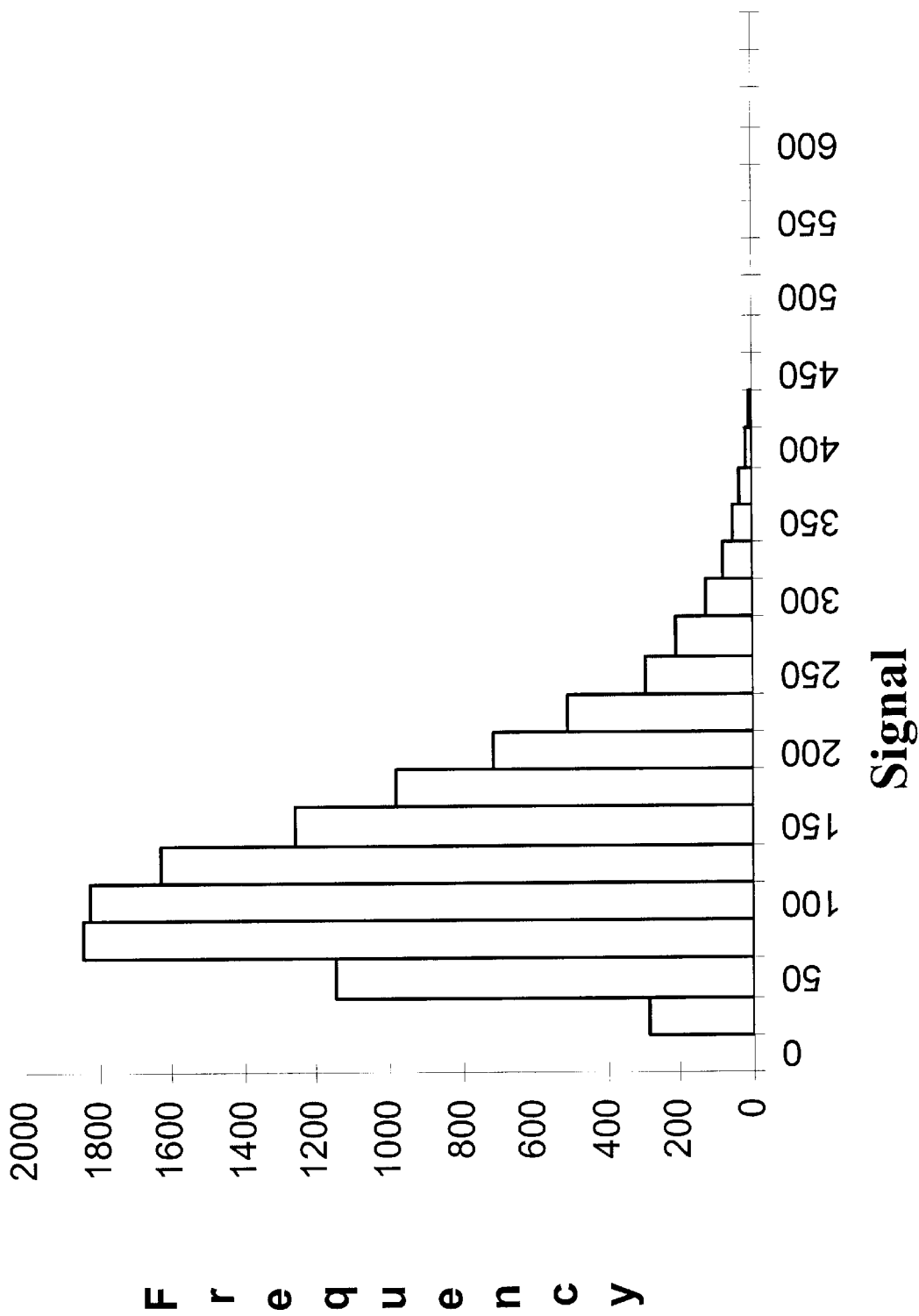

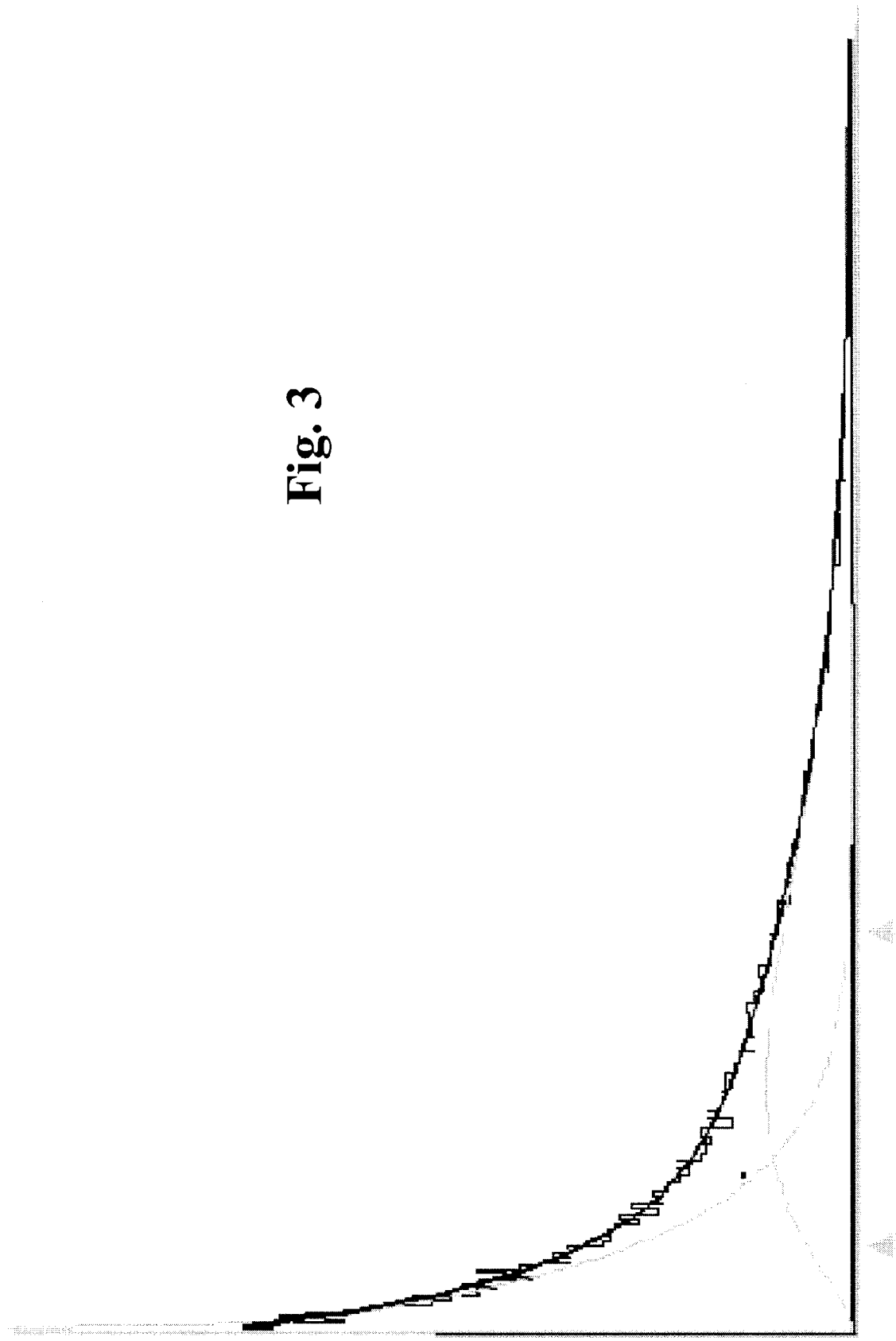

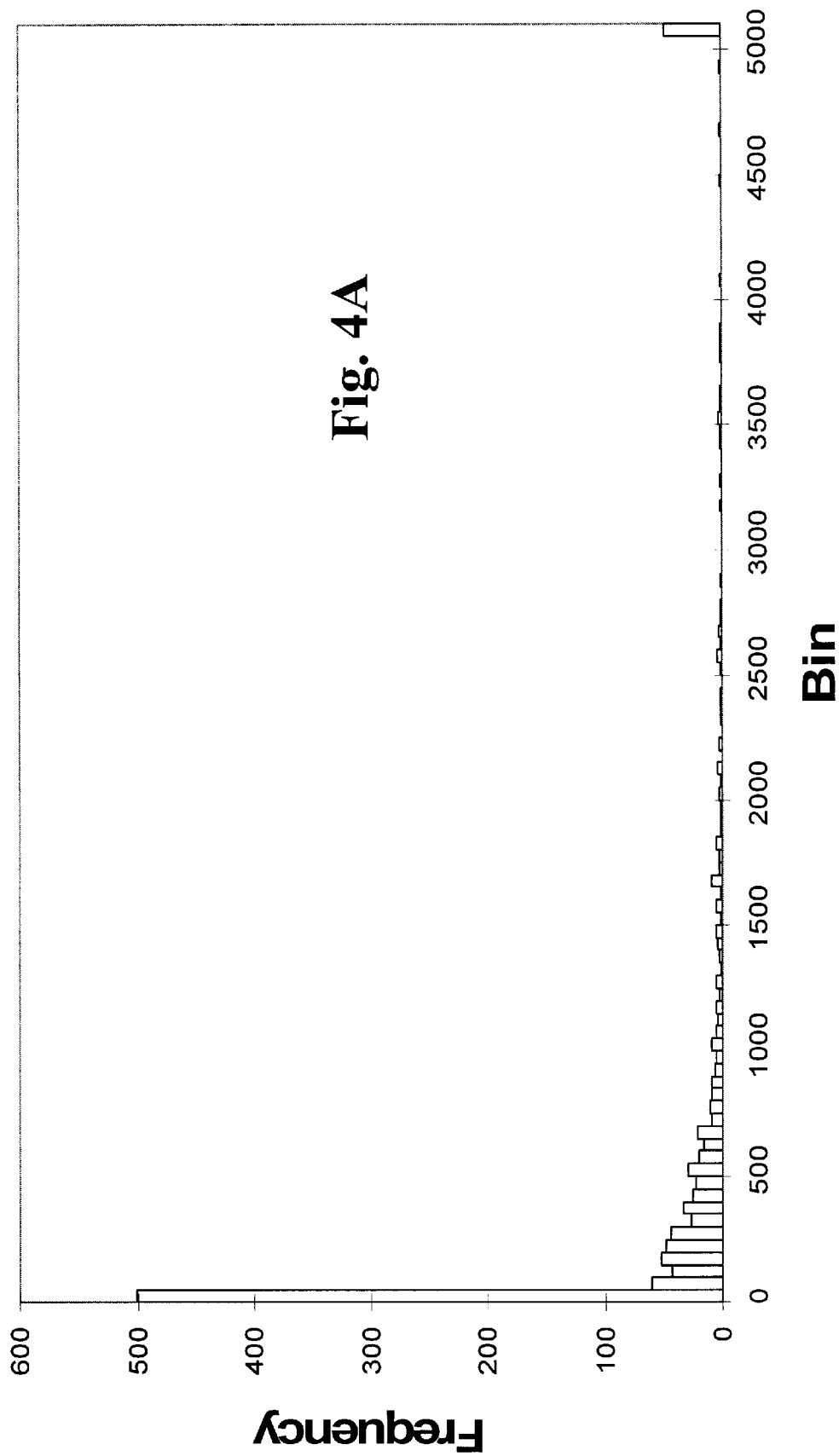

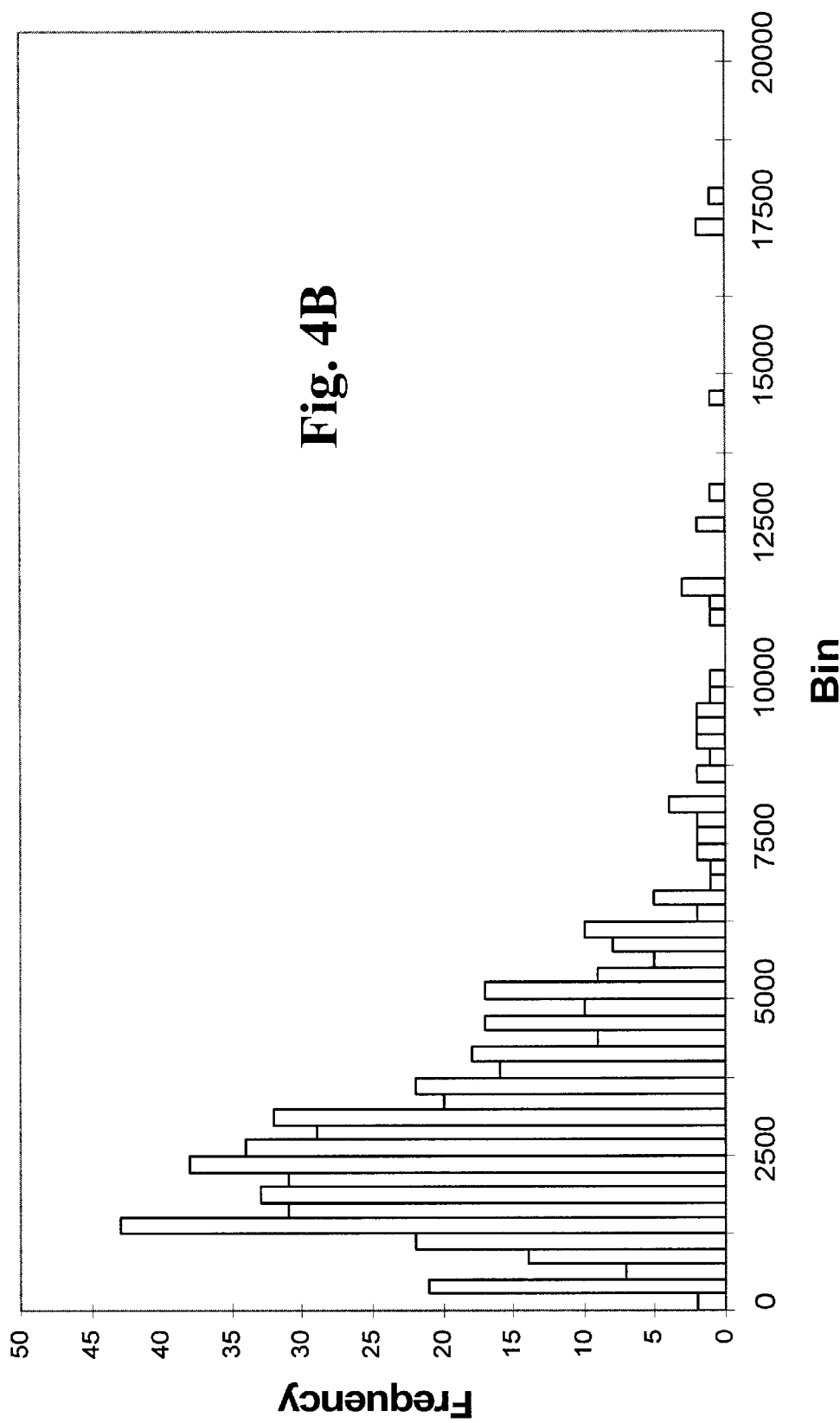

PROCESS FOR EVALUATING CHEMICAL AND BIOLOGICAL ASSAYS

This is a continuation of International Application Serial No. PCT/IB99/00734, filed Apr. 22, 1999 the entire disclosure of which is incorporated herein by reference and claims the benefit of U.S. Provisional Application No. 60/082692, Apr. 22, 1998.

FIELD OF THE INVENTION

The present invention relates to a process for making evaluations which objectify analyses of data obtained from hybridization arrays. The present invention is in one aspect a method for making inferences as to the extent of random error present in replicate genomic samples composed of small numbers of data points, and in another aspect is a method for distinguishing among different classes of probe intensities (e.g., signal versus nonsignal).

BACKGROUND OF THE INVENTION

Array-based genetic analyses start with a large library of cDNAs or oligonucleotides (probes), immobilized on a substrate. The probes are hybridized with a single labeled sequence, or a labeled complex mixture derived from a tissue or cell line messenger RNA (target). As used herein, the term "probe", will therefore be understood to refer to material tethered to the array, and the term "target" will refer to material that is applied to the probes on the array, so that hybridization may occur.

There are two kinds of measurement error, random and systematic. Random error can be detected by repeated measurements of the same process or attribute and is handled by statistical procedures. Low random error corresponds to high precision. Systematic error (offset or bias) cannot be detected by repeated measurements. Low systematic error corresponds to high accuracy.

Background correction involves subtracting from the probe the intensity of an area outside of that probe. Areas used for calculation of background can be close to the probe (e.g. a circle lying around the probe), or distant. For example, "blank" elements can be created (i.e., elements without probe material), and the value of these elements can be used for background estimation.

Normalization procedures involve dividing the probe by the intensity of some reference. Most commonly, this reference is taken from a set of probes, or from the mean of all probes.

Once systematic error has been removed by background removal and normalization procedures (or others, as required), any remaining measurement error is, in theory, random. Random error reflects the expected statistical variation in a measured value. A measured value may consist, for example, of a single value, a summary of values (mean, median), a difference between single or summary values, or a difference between differences. In order for two values to be considered reliably different from each other, their difference must exceed a threshold defined jointly by the measurement error associated with the difference and by a specified probability of concluding erroneously that the two values differ (Type I error rate).

Of primary interest are differences between two or more quantified values, typically across different conditions (e.g., diseased versus non-diseased cell lines, drug versus no drug). The desired estimate of expected random error ideally should be obtained from variation displayed by replicate values of the same quantity. This is the way that such estimates are normally used in other areas of science. Hybridization studies, however, tend to use a very small number of replicates (e.g., two or three). Estimates of random error based on such small samples are themselves very variable, making comparisons between conditions using standard statistical tests imprecise and impractical for all but very large differences.

This difficulty has been recognized by Bassett, Eisen, & Boguski in, "Gene expression informatics: It's all in your mine", *Nature Genetics,* 21, 51–55 (1999), who have argued that the most challenging aspects of presenting gene expression data involve the quantification and qualification of expression values and that qualification would include standard statistical significance tests and confidence intervals. They argued further that "ideally, it will be economically feasible to repeat an experiment a sufficient number of times so that the variance associated with each transcript level can be given" (p. 54). The phrase "sufficient number of times" in the preceding quote highlights the problem. The current state-of-the-art in array-based studies precludes obtaining standard statistical indices (e.g., confidence intervals, outlier delineation) and performing standard statistical tests (e.g., t-tests, analyses-of-variance) that are used routinely in other scientific domains, because the number of replicates typically present in studies would ordinarily be considered insufficient for these purposes. A key novelty in the present invention is the circumvention of this difficulty.

Statistical indices and tests are required so that estimates can be made about the reliability of observed differences between probe/target interactions across different conditions. The key question in these kinds of comparisons is whether it is likely that observed differences in measured values reflect random error only or random error combined with treatment effect (i.e., "true difference")? In the absence of formal statistical procedures for deciding between these alternatives, informal procedures have evolved in prior art. These procedures can be summarized as follows:

1. Arbitrary Thresholds

Observed differences across conditions differ by an arbitrary threshold. For example, differences greater than 2- or 3-fold are judged to reflect "true" differences.

2. Thresholds Established Relative to a Subset of Array Elements

A subset of "reference" genes is used as a comparison point for ratios of interest. For example, relative to the reference gene, a gene may show a 2:1 expression ratio when measured at time 1, a 2.8:1 ratio when measured at time 2, and so on.

3. Thresholds Established Based on Observed Variation in Background

The standard deviation of background values is used as a proxy for the measurement error standard deviation associated with probe values of interest. If a probe intensity exceeds the background standard deviation by a specified number (e.g., 2.5), the probe is considered "significant." None of the above approaches is optimal, because each relies on a relatively small number of observations for deriving inferential rules. Also, assessments of confidence are subjective and cannot be assessed relative to "chance" statistical models. Approaches 1 and 2 are especially vulnerable to this critique. They do not meet standards of statistical inference generally accepted in other fields of science in that formal probability models play no role in the decision-making process. Approach 3 is less subject to this latter critique in that a proxy of measurement error is obtained from background. It is nonetheless not optimal because the measurement error is not obtained directly from the measured values of interest (i.e., the probes) and it is not necessarily the case that the error operating on the background values is of the same magnitude and/or model as the one operating on probe values.

Other informal approaches are possible. For example, the approaches described in 2 above could be modified to estimate the standard deviations of log-transformed measurements of reference genes probed more than once. Because of the equality [log(a)–log(b)=log(a/b)], these proxy estimates of measurement error could then be used to derive confidence intervals for differential ratios of log-transformed probes of interest. This approach would nonetheless be less than optimal because the error would be based on proxy values and on a relatively small number of replicates.

Chen et al. (Chen, Dougherty, & Bittner) in "Ratio-based decisions and the quantitative analysis of cDNA microarray images", *Journal of Biomedical Optics*, 2, 364–374 (1997) have presented an analytical mathematical approach that estimates the distribution of non-replicated differential ratios under the null hypothesis. Like the present invention, this procedure derives a method for obtaining confidence intervals and probability estimates for differences in probe intensities across different conditions. However, it differs from the present invention in how it obtains these estimates. Unlike the present invention, the Chen et al. approach does not obtain measurement error estimates from replicate probe values. Instead, the measurement error associated with ratios of probe intensities between conditions is obtained via mathematical derivation of the null hypothesis distribution of ratios. That is, Chen et al. derive what the distribution of ratios would be if none of the probes showed differences in measured values across conditions that were greater than would be expected by "chance." Based on this derivation, they establish thresholds for statistically reliable ratios of probe intensities across two conditions. The method, as derived, is applicable to assessing differences across two conditions only. Moreover, it assumes that the measurement error associated with probe intensities is normally distributed. The method, as derived, cannot accommodate other measurement error models (e.g., lognormal). It also assumes that all measured values are unbiased and reliable estimates of the "true" probe intensity. That is, it is assumed that none of the probe intensities are "outlier" values that should be excluded from analysis. Indeed, outlier detection is not possible with the approach described by Chen et al.

The approaches described above attempt to address issues that relate to how large differences across conditions must be before they are considered sufficiently reliable to warrant a conclusion of "true" difference. Distinguishing between probe values that represent signal and those that represent nonsignal represents a different issue which relates to the qualification of probe values within arrays rather than across conditions.

Two approaches have been presented Piétu et al. (Piétu, Alibert, Guichard, and Lamy), observed in "Novel gene transcripts preferentially expressed in human muscles revealed by quantitative hybridization of a high density cDNA array", *Genome Research*, 6, 492–503 (1996) in their study that a histogram of probe intensities presented a bimodal distribution. They observed further that the distribution of smaller values appeared to follow a Gaussian distribution. In a manner not described in their publication, they "fitted" the distribution of smaller values to a Gaussian curve and used a threshold of 1.96 standard deviations above the mean of the Gaussian curve to distinguish nonsignals (smaller than the threshold) from signals (larger than the threshold).

Chen et al. (cited above) describe the following method for assessing whether a probe represents a signal or nonsignal value. Within a digitized image of an array, pixels within each probe area are rank-ordered. The intensity of the eight lowest pixel values is compared to background via a nonparametric statistical test (Mann-Whitney U-test). If results of the statistical test supports the conclusion that these eight pixel values are above background, the procedure stops and the probe is considered a signal. If the eight pixel values are not above background, some or all of the pixels are considered to be at or below background. The same test is repeated by either eliminating all eight pixels and repeating the test with the next eight lowest pixel values or by eliminating a subset of the eight pixels and replacing them with the same number of the next lowest values. The test proceeds in this fashion until all pixels are estimated to be at or below background or until a threshold of number of pixels is reached. In either case, the probe is classified as nonsignal.

The macro format (FIGS. 1,4) was introduced some years ago and is in fairly widespread use. Typically, probes are laid down on membranes as spots of about 1 mm in diameter. These large spots are easily produced with robots, and are well suited to isotopic labeling of targets, because the spread of ionizing radiation from an energetic label molecule (e.g. 32P) precludes the use of small, closely-spaced probes. Detection is most commonly performed using storage phosphor imagers.

Microarrays consisting of oligonucleotides synthesized on microfabricated devices have been in use for some time. With the recent commercial availability of microarraying and detection apparatus, microarrays of single-stranded cDNAs deposited on are seeing broader use.

With both micro and macro genome arrays, numerical data are produced by detecting the amount of isotope or fluorescent label at each assay site. The result is one or more arrays of numbers, each member of which quantifies the extent of hybridization at one assay in the specimen array. The hybridization level is an indication of the expression level of sequences complementary to a specific probe. Therefore, analysis can be used to both identify the presence of complementary sequences, and to quantify gene expression leading to those complementary sequences.

The analysis proceeds by determining which specific assays show interesting alterations in hybridization level. Typically, alterations in hybridization are specified as ratios between conditions. For, example, data may be of the form that assay X (representing expression of a particular gene) is three times as heavily labeled in a tumor cell line as in a normal cell line. The relevant issue is "how is the statistical significance of a specific comparison to be specified?"

Specification of statistical significance is important because of the presence of error in our measurements. We could define true hybridization as the amount that would be observed if procedural and measurement error were not present. Ideally, the same probe-target pairing would always give us the same measured hybridization value. Valid hybridization values are those which index true hybridization.

In fact, hybridization tends to be heavily influenced by conditions of the reaction and by measurement error. The mean coefficient of variation in a replicated fluorescent microarray often hovers near 25%. That is, repeated instances of hybridization between the same probe and target can yield values which vary considerably about a mean (the best estimate of true hybridization). Therefore, any single data point may or may not be an accurate reflection of true hybridization.

The present invention differs from prior art in that it estimates measurement error directly from array replicates (within or across arrays). The present invention is able to provide statistically valid inferences with the small numbers of replicates (e.g., three) characteristic of array hybridization studies. In the present invention, the statistical difficulties posed by small sample sizes are circumvented by the novel process of obtaining an estimate of measurement error for each probe based on the average variance of all replicates for all probes. In accordance with one preferred aspect, the invention assumes that all replicates, being part of the same population of experiments and being similarly treated during array processing, share a common and/or constant variance.

In accordance with another preferred aspect, measurement error can be assessed separately for different probe classes. These classes may be determined based on the deconvolution procedures described below or by other statistical or experimental methods.

The present invention differs from all prior art in that it:
1. is applicable to any number of experimental conditions rather than being restricted to only two conditions;
2. estimates measurement error empirically from probe replicates;
3. can detect outliers;
4. can accommodate various measurement error models; and
5. can assess the adequacy of an assumed measurement error model.

There is a second aspect to the present invention, which deals with the discrimination of probe response classes within arrays. Element measurements within arrays may reflect multiple classes of values. For example, some values may represent signals and others may represent nonsignals (e.g., background). As another example, some values may represent a family of genes associated with disease states, while other values originate from genes not known to be altered in disease. The present invention is novel in that it uses a mathematically-derived approach for deconvolving any mixture of distinct underlying distributions, which is used in turn to classify probe values as signal or nonsignal.

Specifically, the present invention is novel in its method of treating overlapping distributions within the arrayed data. In particular, the invention models dual or multiple distributions within an array. Preferably, it does this by mathematical mixture modeling which can be applied to deconvolve distributions and regions of overlap between distributions in a rigorous fashion. This contrasts with prior art, which fails to model more than one distribution with array data and which, therefore, is unable to model regions of overlap between distributions. As a consequence, prior art may miss data (e.g., probes with low signal levels) which have acceptable probabilities of belonging to a valid signal distribution. The present invention assigns probabilities that any probe belongs to one of the contributory distributions within an array data population.

BRIEF DESCRIPTION OF THE DRAWINGS

Further objects, features and advantages of the invention will be understood more completely from the following detailed description of a presently preferred, but nonetheless illustrative embodiment, with reference being had to the accompanying drawings, in which:

FIG. 2, comprising FIGS. 2A and 2B, shows discrete distributions of signal and nonsignal modeled from the data set in FIG. 1.

FIG. 3 shows both distributions from FIG. 2, with the region of overlap within which the modeling process attributes the origin of data points.

FIG. 4, comprising FIGS. 4A and 4B, shows a frequency distribution of expression values from a lymphocyte cell line (each assay is the mean of three replicates) on a glass microarray, and a Clonetech Atlas array on a nylon membrane. Background from the substrate has been subtracted, in both cases. The glass array shows a relatively small proportion of values lying in a region that might be confused with nonspecific hybridization. The membrane array shows a large peak in the background region. The membrane array is a suitable subject for modeling. The glass array may not be.

DESCRIPTION OF THE PREFERRED EMBODIMENT

The present invention is a statistical procedure for objective analyses of array data. It includes two processes.

a) Deconvolution of distributions. Where the observed data array includes contributions from two or more distributions, the present invention deconvolves those distributions into discrete probability density functions. This allows discriminating of hybridization signal from nonsignal, and/or discriminating contributions of one label from another;

b) Attributing confidence to assays.

Our treatment of how distributions are discriminated will refer to a data set composed of signal and nonsignal. Application of these procedures to a data set containing contributions of two or more labels will be obvious to one skilled in the art.

Figure 1:
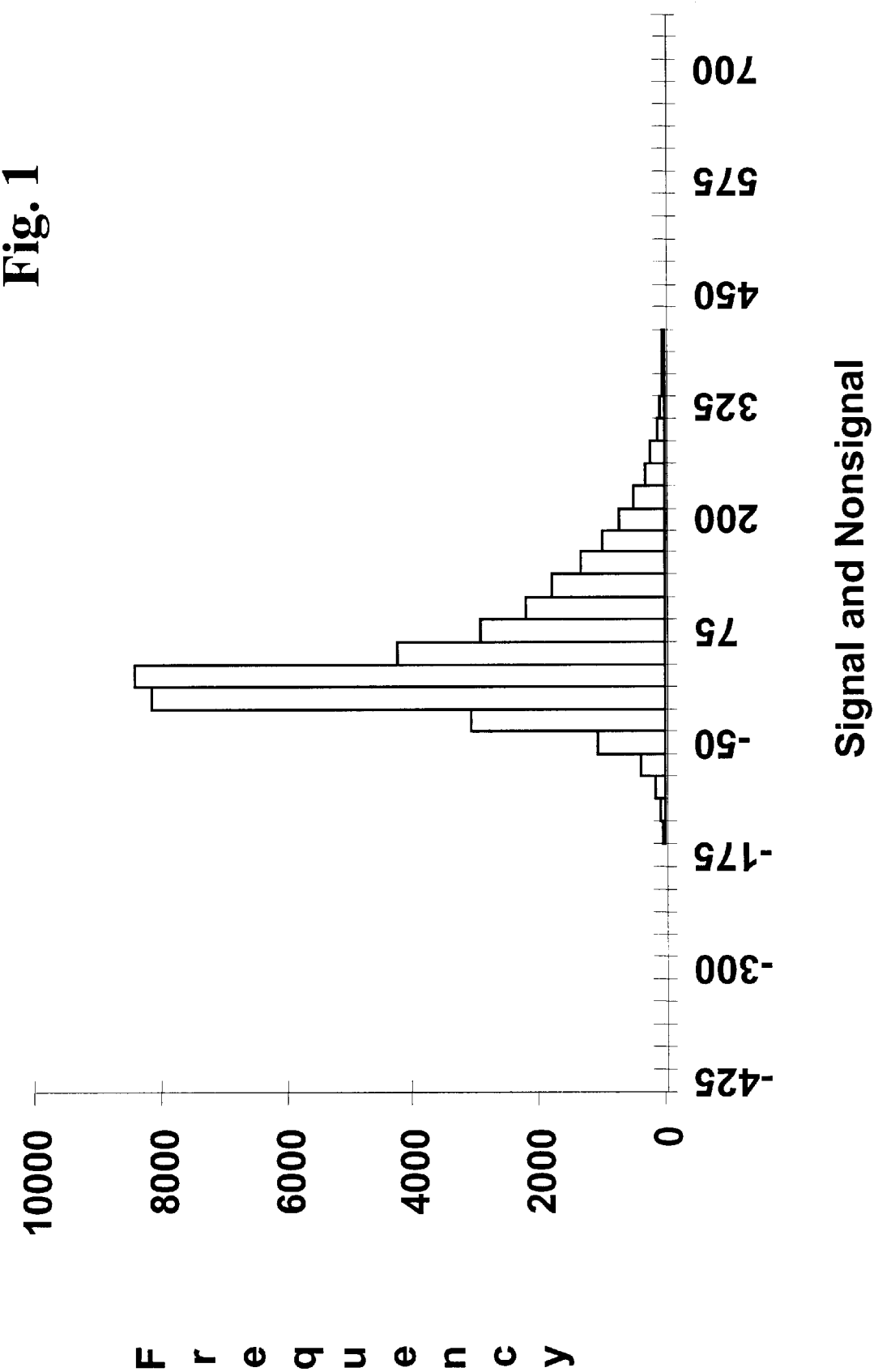
FIG. 1 is a frequency distribution of a simulated hybridization array, showing a mixture of both signal and nonsignal assays. Background has a mean of zero, and varies about that value. Therefore, there are both positive and negative values in the distribution. This type of distribution is typical of those found in nylon arrays.

A hybridization data set provides both signal and nonsignal elements (FIG. 1). Discrimination of nonsignal is necessary so that we can make meaningful comparisons of expression (signal:signal), while avoiding spurious comparisons (any that include nonsignal).

Figure 2A:
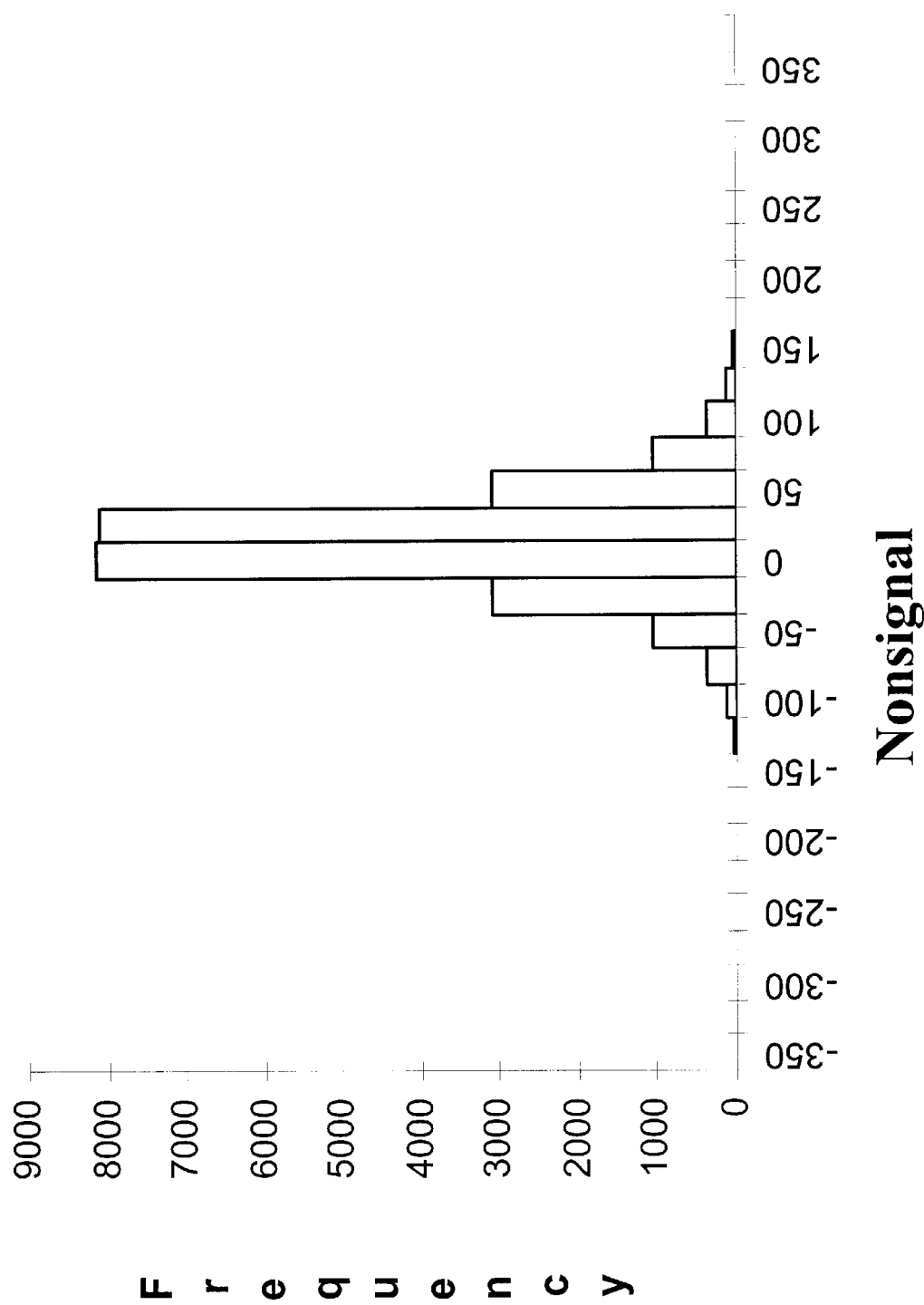

Assume the presence of one or more distributions. The first issue is setting the threshold for signal. Our procedure uses information derived from the variance properties of the array, to define the cutoff point between nonsignal and signal. First, we assume that the array distribution is actually a mixture of two distributions. These are a distribution in the lower intensity range (nonsignal, including background and nonspecific hybridization) and a distribution in the higher intensity range (signal) (FIG. 2).

Describe Probability Density Functions for the Two Distributions, Using Modeling We now create a set of descriptors, that will specify the nature of each distribution. To create these descriptors, we make another assumption. The assumption is that each distribution originates from a specific probability density function (pdf) which can be estimated from four parameters—means, variance, proportion of the mixture, and class (e.g. Gaussian, gamma). A well-accepted method for deriving mean, variance, and proportion of mixture from mixed distributions is maximum likelihood estimation (MLE). Other methods could be used.

Definitions

Maximum Likelihood Method

We ask, "How likely is it that we would have obtained the actual data given values (generated by software or the user) for four parameters for each distribution (mean, variance, proportion of mixture, and distribution class?" (e.g. Gaussian, gamma). The MLE procedure estimates the likelihood of obtaining the actual data given the initial values, and then proceeds to evaluate this likelihood given slightly different values. Iteration continues until it arrives at a likelihood that is at its maximum or until predefined iteration limit is reached.

Probability Density Function

A curve (e.g., Gaussian) defined by a mathematical equation. Probabilities for ranges of values (e.g., $x \leq 100$; $x \geq 500$) can be derived based on area under the curve.

The MLE procedure generates pdfs for the signal and nonsignal distributions (FIG. 3). These distributions include areas that are unambiguously part of one distribution or another. hey also contain an area of overlap, and it is, in this overlap area that our process operates to assign the origin of data points.

Use the Probability Density Function to Assign Hybridization Values to Their Distribution of Origin For any hybridization value, we can determine the probability of obtaining a value that large or larger from the nonsignal distribution or that small or smaller from the signal distribution. In this way, we obtain two probabilities (one that the value came from the nonsignal distribution and one that the value came from the signal distribution). Comparing the two probabilities tells us which distribution is the more likely originator of the data value.

Consider the values reported in Table 1, which were taken from the simulated data discussed in Appendix A. There are three things to note:

1. Higher values are less likely to have come from the nonsignal distribution (see Column 2) and more likely to have come from the signal distribution (see Column 3).
2. The probabilities in Columns 2 and 2 show which of the two distributions is more likely to be the origin of a particular hybridization value. For example, the probability that a value of 40 or greater came from the nonsignal distribution is 0.2107. The probability that a value of 40 or less came from the signal distribution is 0.0995. Our procedure establishes that a value of 40 is more likely to have come from the nonsignal distribution.
3. A criterion value for signal and nonsignal hybridization can be obtained from the probability function. In our example, a value less than or equal to 49 is categorized as nonsignal and greater than 49 is categorized as signal.

TABLE 1

Probabilities of origin for various hybridization values.

| Value | Probability of Originating from the Nonsignal Distribution | Probability of Originating from the Signal Distribution | More Likely Originating Distribution |
|---|---|---|---|
| 40 | .2107 | .0995 | Background |
| 45 | .1740 | .1258 | Background |
| 49 | .1493 | .1482 | Background |
| 50 | .1436 | .1540 | Signal |
| 60 | .0980 | .2148 | Signal |
| 70 | .0669 | .2788 | Signal |

Test Goodness of Fit

The present invention creates models which purport to describe real data. We can evaluate the models using a goodness of fit parameter based on the chi-square statistic. The test can be automated, and the software flags cases in which the modeling results in a bad fit.

When Modeling Is Appropriate

The modeling procedure assumes that the array of hybridization data points can be parsed into multiple distributions, each with sufficient members to allow accurate modeling. This is usually the case with nylon arrays, which contain large nonsignal components (FIG. 4). Many glass arrays are quite different in nature. The background tends to be much lower, and the signal to noise higher. Therefore, it may not be possible or necessary to model a nonsignal distribution for very clean arrays. In the case of a clean glass array with a single label, we can assume a single (signal) distribution, dispense with the modeling, and use a simple signal criterion to discriminate usable assays (e.g. assays with a signal to noise ratio>3:1).

Summary of Distribution Modeling

The present invention uses modeling procedures to deconvolve a data matrix into two or more probability density functions. Hybridization data are then assigned to the most likely distribution of origin. Advantages of the present invention are that the modeling procedure provides an objective method for assigning hybridization values to signal or nonsignal distributions, to one label or another, or to any other deconvolved distributions. The process can include a goodness of fit test, which alerts us if the outcome of the modeling is suspect.

Attributing Confidence

Any hybridization assay is an estimate. That is, if we repeat the assay a number of times, we will obtain values which vary about a mean. All of these values estimate a true hybridization value. Some assay values are good estimates of the true value, and others are not. Poor estimates cover a broad range of potential true values. Good estimates cover a narrow range. In defining confidence limits, the present invention generates ranges around the observed values. We can have high confidence (e.g. >95%) that the true values lie within these ranges. We can also use these ranges to determine our confidence in differences between assay values. If the ranges overlap, we have low confidence in the differences. If the ranges do not overlap, we have high confidence. Therefore, the present invention provides confidence scores for each case of differential hybridization (see next section).

Point 1: User Entry of Error Estimate

We obtain an error magnitude in one of two ways. If we are dealing with single member arrays (no replicates), the user can enter an estimate of how much error (as a proportion or constant) is present. For example, housekeeping genes might tell us that this assay has a measurement error of 25%.

Point 2: Determination of Error from Replicates Using Standard Deviation or Coefficient of Variation Measurement error can also be determined, directly, from replicates. The advantage of the replicate procedure is that the error associated with an average is decreased by a factor of $1\sqrt{n}$ where n is the number of replicates. We can use information regarding this variability to provide an overall validity parameter for the entire array (eq. 1).

$$\sigma_x = \sqrt{\frac{\sum (x - \bar{x})^2}{N - 1}} \quad (1)$$

where N is the number of replicates.

The coefficient of variation is a useful measure of variability, for measures that have proportional measurement error (characteristic of hybridization arrays). The percentage measurement error associated with an individual value (relative to its mean) is estimated as:

$$Percentage\ CV_x = 100 \frac{\hat{\sigma}_x}{\bar{x}}$$

Point 3: Identify Highly Unreliable Assays Using Estimates of Variance Derived from the Replicates Estimates of variability across replicates will vary from assay to assay. If they vary too much, the assay should be discarded. How do we set the criterion for discarding an assay?

We examine the variability of the variability. From this, we can identify replicates whose variability exceeds a value. The value is determined by calculating the variance of the variance values, and setting an objective variance criterion (e.g. 3 SD units) to indicate outliers.

In the case of additive error (e.g., 100±10, 1000±10), the standard deviation is the best estimator of variance around each data point. The absolute value of error remains constant.

In the case of proportional error (e.g., 100±10, 1000±100), the coefficient of variation is a more useful measure of variability. The standard deviation changes proportionally to the magnitude of the measurement value.

Raw score hybridization assays will, typically, present proportional error, whereas log transformed assays will present additive error. The appropriate statistic is chosen on that basis.

To summarize the process, we obtain an average SD or CV for the replicates in the entire array. We then use that average in the next step.

For an additive error model, this averaging process is accomplished by Equation 2:

$$\hat{\sigma}_g^2 = \frac{1}{n} \sum_{i=1}^{n} \sum_{j=1}^{m} (y_{gij} - \bar{y}_{gi})^2 / (m - 1) \quad (2)$$

where the subscript g refers to a group or condition (e.g., drug, control). Two groups are modeled here for illustrative purposes, although the discussion generalizes to any number of groups. The subscript i refers to an arrayed probe (n is the total number of arrayed probes), and the subscript j refers to replicate (m is the number of replicates). Equation 2 is a key property of the present invention, in that it describes the method by which variance properties of discrete replicate groups can be estimated from those of the entire array. This method estimates the expected value of the population variance, given the observed data. Other methods which use information based on the variance across replicate sets for the entire array are possible (e.g., Maximum Likelihood Method). This latter method calculates, for different values of $\hat{\sigma}_g^2$, the likelihood of obtaining the observed data. The estimate of $\hat{\sigma}_g^2$ which produces the highest likelihood is chosen as the estimate of the population variance. In either method, the novelty derives from the use of the variance across replicates for the entire array in choosing the population variance value that is then applied to each of the replicate sets.

Point 4. Use the Confidence Limits Derived from the Entire Array or a Set of Reference Assays to Estimate the Variability of Individual Assay Values The percentage CV provides a measure of the variability of the individual replicate values around their mean. The mean of replicates is the best estimate of the assay's true value. However, the mean value has measurement error associated with it. The standard deviation associated with a mean value is called a standard error of the mean and is calculated as:

$$\hat{\sigma}_{\bar{x}} = \frac{\hat{\sigma}_x}{\sqrt{N}}$$

where N is the number of replicates.

When measurement error is proportional, a measure of variability is the percentage CV for the mean, which is calculated as:

$$Percentage\ CV_{\bar{x}} = 100 \frac{\hat{\sigma}_{\bar{x}}}{\bar{x}}$$

The present invention takes replicate assays, and calculates measurement error from the replicates. This procedure works well under the assumption of equal CVs or SDs across most or all of the range of assay values. Moreover, assays with unusually high percentage CVs or SDs can be examined and deleted from further analysis if they are deemed to be unreliable.

The Case of Differential Expression Across Arrays

Most modeling processes require large numbers of data points. In some instances, comparing hybridization values across arrays does not provide large numbers of differentially hybridized assays. Rather, there can be a large number of assays with similar ratios (usually 1:1), and only a few cases of differential hybridization (e.g. 4:1). With ratio of hybridization across arrays, the present invention uses forms of distributional modeling that do no require large numbers of data points.

Generate Confidence Limits for Hybridization Ratios, when Replicates Are Present If we have estimates of the percentage errors associated with ratio numerator and denominator, it is a simple matter to estimate the percentage error associated with the ratio according to the following formula:

$$Percentage\ error\ A/B = 100 \sqrt{\left(\frac{\hat{\sigma}_{\bar{x}_A}}{\bar{X}_A}\right)^2 + \left(\frac{\hat{\sigma}_{\bar{x}_B}}{\bar{X}_B}\right)^2}$$

where $\hat{\sigma}_{\bar{x}_A}/\bar{X}_A$ is the proportional error for the replicate means Array A. The present invention uses this formula to calculate the confidence limits for any A/B ratio.

Estimate Confidence Limits for Hybridization Ratios when Replicates Are Not Present The present invention has the advantage that single case assays can be assigned confidence limits. This estimate can be entered by the user. Assign limits on the basis of a variability estimate entered by the user.

Example of The Process
Measurement Error Model Known

In one preferred aspect, the present invention assumes that systematic error has been minimized or modeled by application of known procedures (e.g., background correction, normalization) as required. In another preferred aspect, the present invention could be used with systematic error that has been modeled and thereby removed as a biasing effect upon discrete data points. The process could also be used with unmodeled data containing systematic error, but the results would be less valid.

To facilitate exposition, the following discussion assumes that probes are replicated across arrays. The process applies, equally, however, to cases in which replicates are present within arrays.

Two common error models are "additive" and "proportional." An error model with constant variance, regardless of measured quantity, is called an "additive model." An error model with variance proportional to the measured quantity is called a "proportional model." This latter model violates the assumption of constant variance assumed by many statistical tests. In this case, a logarithm transformation (to any convenient base) changes the error model from proportional to additive. In the process here discussed, a logarithm transformation may be applied to each individual array element. Other transformations or no transformation are envisaged, depending on the error model.

Figure 5:
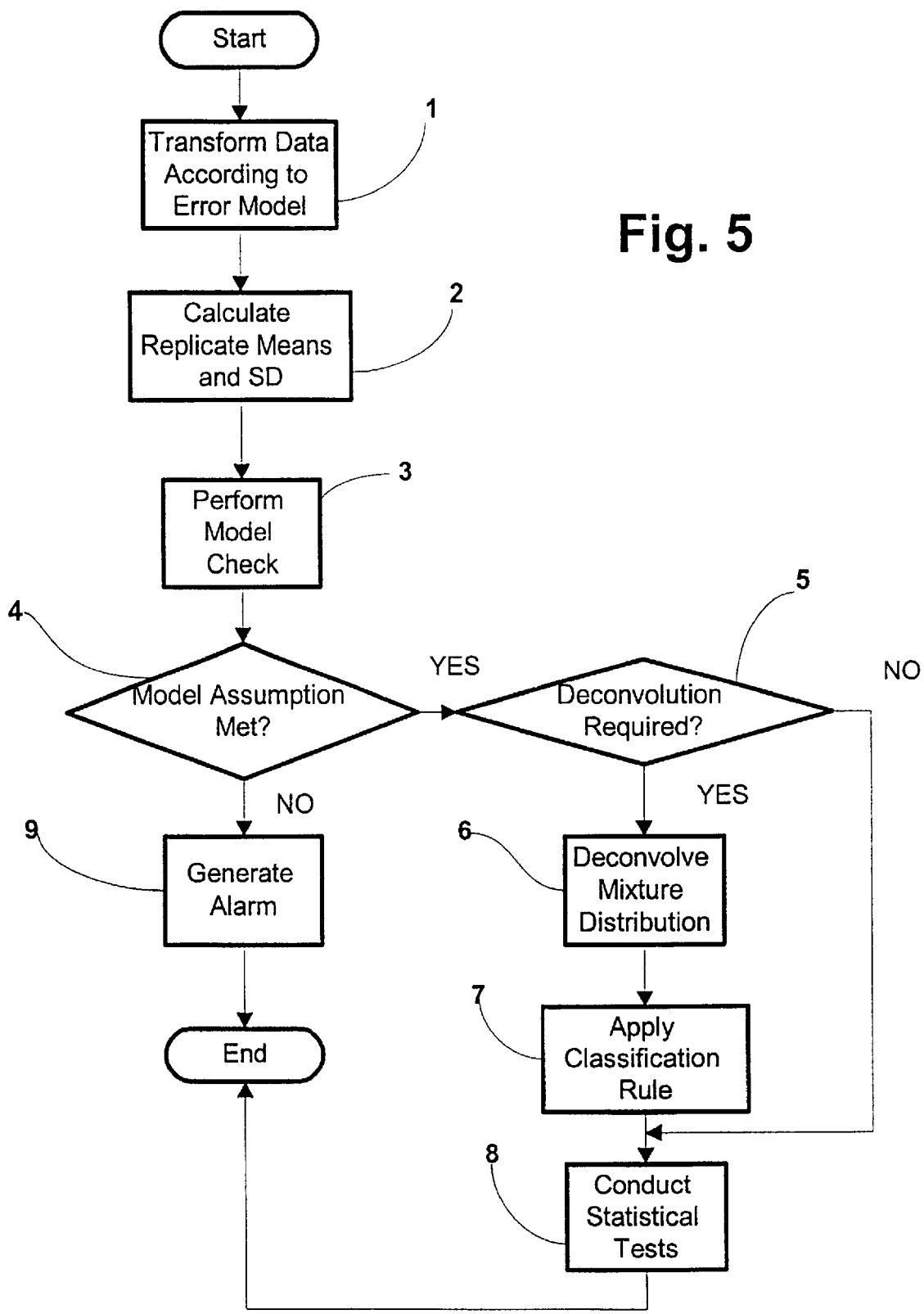
FIGS. 5 and 6 are flowcharts showing a preferred embodiment of the process, with FIG. 5 applying to the instance in which the measurement error model is known and FIG. 6 applying to the instance in which it is not.
Figure 6:
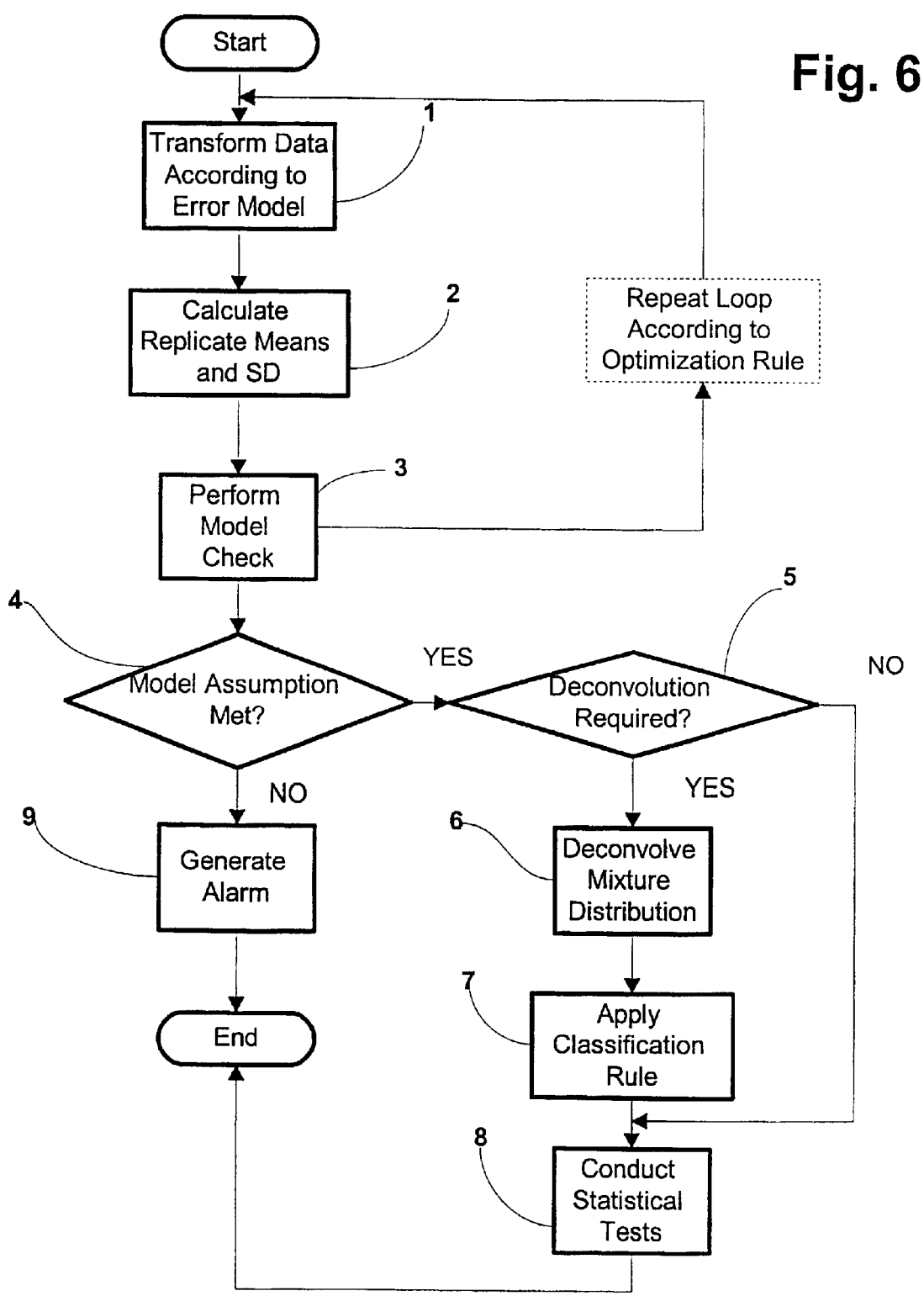

FIGS. 5 and 6 are flow charts illustrating preferred embodiments of the process. Other sequences of action are envisioned. For example, blocks 5 through 7, which involve the deconvolution and classification procedures, might be inserted between blocks 2 and 3. That is, in this alternate embodiment, deconvolution would precede replicate measurement error estimation. An overview of the process when the measurement error model is known is shown in FIG. 5. The paragraphs below are numbered to correspond to the functional block numbers in the figure.

1. Transform data according to error model

In block 1, the raw data are transformed, if necessary, so that assumptions required for subsequent statistical tests are met.

2. Calculate replicate means and standard deviations

Each set of probe replicates is quantified (e.g., by reading fluorescent intensity of a replicate cDNA) and probe values are averaged to generate a mean for each set. An unbiased estimate of variance is calculated for each replicate probe set, as are any other relevant descriptive statistics.

3. Perform model check

In a key aspect of the present invention, average variability for each set of replicates is based on the variability of all replicate sets within the array. This statistic can then be used in diagnostic tests. Various error models and diagnostic tests are possible. Diagnostic tests include graphical (e.g., quantile-quantile plots to check for distribution of residuals assumptions) and formal statistical tests (e.g., chi-squared test; Kolmogorov-Smirnov test; tests comparing mean, skewness, and kurtosis of observed residuals relative to expected values under the error model). If the assumptions of the error model are satisfied, thresholds can be established for the removal of outlier residual observations (e.g., ±3 standard deviations away from the mean). The assumptions of the model can be re-examined with the outliers removed and the average variability for each replicate set can be recalculated. This variability measure can then be used in block 8.

4. Model assumptions met?

In block 4, a judgement is made as to whether the distribution of residuals is adequate to proceed with the data analysis. If yes, we proceed to block 5. If no, we proceed to block 9.

5. Deconvolution required?

In block 5, a decision is made as to whether deconvolution of a mixture distribution of values may be required. If required, we proceed to block 6. If not required, proceed to block 8.

6. Deconvolve mixture distribution

In a key aspect of the present invention, the input data for this process are the element intensities taken across single observations or (preferably) across replicates. In a preferred aspect, the E-M algorithm and any modifications which make its application more flexible (e.g., to allow the modeling of nonnormal distributions; to allow the use of a priori information, e.g., negative values are nonsignal) provides a convenient algorithm for modeling underlying distributions. Other approaches to mixture deconvolution are possible.

7. Apply classification rule

Given the parameters of the distribution obtained in block 6, it will be of interest to classify observations as falling into one class or another (e.g., signal and nonsignal). Observations may be classified according to the procedure described in the section entitled "Use the probability density function to assign hybridization values to their distribution of origin."

8. Statistical Tests

Once measurement error has been determined, standard statistical tests are conducted and confidence intervals are provided. Such tests would include dependent and independent t-tests and dependent and independent analyses of variance (ANOVA) and other standard tests. These comparisons would be made between replicate means from different conditions. Other tests are possible. Upon completion of the tests, the process ends. This is considered to be a normal termination.

9. Generate Alarm

If error model assumptions are not met, an alarm is generated, and the process ends. This is considered to be an abnormal termination. Three solutions are then possible. Raw data may be transformed manually by the Box-Cox or other procedures. The process could be started anew, so that the assumptions of a new model may be assessed. Alternatively, the optimization strategy shown in FIG. 6 could be applied. Finally, the error distribution could be estimated by empirical non-parametric methods such as the bootstrap or other procedures.

Measurement Error Model Not Known

When the measurement error model is unknown, the process, as represented in FIG. 6. is identical to the one used when the error model is known except in how the error model is chosen. In this instance, the error model is chosen based on a computer intensive optimization procedure. Data undergo numerous successive transformations in a loop from blocks 1 through 3. These transformations can be based, for example, on a Box-Cox or other type of transformation obvious to one skilled in the art. The optimal transformation is chosen based on the error model assumptions. If the optimal transformation is close to an accepted theoretically-based one (e.g., log transform), the latter may be preferred. The process proceeds through the remaining steps in the same manner as when the error model is known.

Attached as APPENDIX A is a technical paper which discloses further aspects of preferred embodiments of the invention.

Although a preferred embodiment of the invention has been disclosed for illustrative purposes, those skilled in the art will appreciate that many additions, modifications and substitutions are possible without departing from the scope and spirit of the invention.

APPENDIX A

Statistical Informatics

Procedures for Analyses of Array Data

Introduction ........................................................................................................................... 25
   Classes of Expression Study ............................................................................................ 25
   Expression Data ............................................................................................................. 25
   A New Procedure ........................................................................................................... 26

Discriminating Distributions ................................................................................................ 27
   The Modeling Process .................................................................................................... 28
   When Modeling is Appropriate ....................................................................................... 29
   Modeling a Real Specimen ............................................................................................. 30
   Summary of Distribution Modeling ................................................................................. 32

Reliability and Confidence Intervals .................................................................................... 32
   The Process: Replicates Are Present ............................................................................... 32
   The Process: Replicates Are Not Present ........................................................................ 34

Analyzing Differential Expression ........................................................................................ 34
   The Process: Measurement Error Known ........................................................................ 34
   The Process: Measurement Error Unkown ...................................................................... 34
   A Graphical Option ........................................................................................................ 36

References ............................................................................................................................. 37

Introduction

Array-based expression analysis (ABEx) is projected to find increasing application in drug discovery and diagnostics. Although ABEx tools remain complex, our belief is that we are entering a period in which a rapid evolution of skills and commercial tools will favor increased application of this technology.

Some of the ABEx evolution will lie in materials, processes, and instrumentation. Advances will be made in microfabrication, hybridization procedures, arraying and detection. Another evolving aspect relates to the ways in which meaning is extracted from the arrays - informatics. Questions regarding meaning are posed at two levels.

- Validity of observations. How do we verify that our observations are real?
- Consequential validity. Do our observations have meaning in terms of biological consequences for the organism? For example, can we identify consistent "expression patterns" in families of genes that show similar activity under conditions of interest? Can alterations in expression of specific genes be linked to translational/post-translational events?

All ABEx users will face both these questions. Consequential validity is the goal of the research. Verified observational validity is a precondition to drawing conclusions regarding consequential validity.

We believe that complete ABEx systems must both detect and specify validity for high density arrays of hybridization data. Therefore, we are developing tools for "statistical informatics". Statistical informatics (SI) is a set of analytical procedures that provide reliability estimates of ABEx data points. Statistically reliable data are more likely to be valid.

Classes of Expression Study

ABEx studies fall into three general classes.

| | |
|---|---|
| Single condition: | Expression in a single condition, without comparison to control. |
| Diagnostic: | Expression in a single condition, with comparison to a standard control. |
| Comparative: | Direct comparisons of expression across conditions. |

Single condition studies (e.g. Pietu et al., 1996) make reports of the order "We found X highly expressed sequences in this tissue, some of which are not expressed in other tissues". These types of reports are becoming less common, because it is very difficult to establish a causal link between an expression observation and a tissue condition.

Diagnostic and comparative studies perform direct comparison of specimen conditions. In the diagnostic case, the comparison is with an independently standardized control condition. In the comparative case, multiple conditions are included within an experiment.

Expression Data

All classes of ABEx study must yield reliable expression values. Note that the term reliable, as used here, is analytical as opposed to biological. Reliable expression values are those which have a specified (and preferably low) error variance. There are various strategies used to decrease error variance in array data.

- Multiple spotting. Replication (using multiple instances of each probe) paradigms have long been used to minimize effects of variation within an assay. By using multiple replicates of an assay and taking an average, or excluding highly variable cases, we achieve a more reliable result than if we take a single case.

- Fluorescent label. A very large improvement in data quality can be obtained by moving from isotopically labeled specimens on nylon membranes to fluorescently labeled specimens on glass substrates.
- Comparing conditions using multiple labels on the same probe. Multiple fluorescent labels minimize error variance by allowing direct comparisons between different conditions (e.g. cancer vs. normal) hybridized to a single probe (e.g. DeRisi et al., 1996; Shalon, Smith and Brown, 1996). In this case, data are expressed as ratios between conditions.
- Reference the mean, median, or a set of reference genes. Each member of the array may be referenced to some global parameter. Theoretically, this process will minimize intersample variation by removing reliance on absolute intensity values.
- Match-mismatch pairs. Each sequence in the array has a companion that differs, usually by one base pair. Data are expressed as a ratio of the "perfect match" to the mismatched sequence or as a subtracted value (match - mismatch). Subtraction removes nonspecific hybridization and background (which should be the same under both conditions), and normalization provides an internal reference for the probe in question.

Once we have produced a body of data, the next step is specification of how much alteration in expression is meaningful. For example, one sees statements such as "2:1 alterations in expression are detectable". The precise justification for this type of statement varies. The most common approach uses an estimate of variability derived from reference genes. The library contains a set of reference or "housekeeping" genes, which are known to hybridize. Variance in this set is used to establish a variance criterion for other members of the array.

A New Procedure

We propose a statistical procedure, which we call "statistical informatics" (SI), for analyses of ABEx data. SI includes two major components.

a) Deconvolution of distributions. If the array data include contributions from two or more distributions (e.g. signal/nonsignal, multiple fluors), we deconvolve those distributions into distinct probability density functions. This allows discriminating of hybridization signal from nonsignal, and/or discriminating contributions of one label from another;

b) Reliability of expression values. Some of our observed expression values are good estimates (reliable). Others are heavily influenced by error (unreliable). For any expression value, we calculate reliability.

Advantages of SI include:

- accept data generated using any variance reduction strategies;
- model-based, as opposed to using reference materials created with the array;
- are simple to use, in that generic arrays can be analyzed;
- provide an objective method for calculating the reliability of each data point.

Discriminating Distributions

Many ABEx data arrays are composed of multiple distributions. For example, a hybridization data set provides both signal and nonsignal elements (Figures 1,2). Discrimination of nonsignal is necessary so that we can make meaningful comparisons of expression (signal:signal), while avoiding spurious comparisons (any that include nonsignal).

*Figure 1: Frequency distribution of a simulated array, showing a mixture of both signal and nonsignal assays. Background has a mean of zero, and varies about that value. Therefore, there are both positive and negative values in the distribution. This type of distribution is typical of arrays on nylon membranes.*

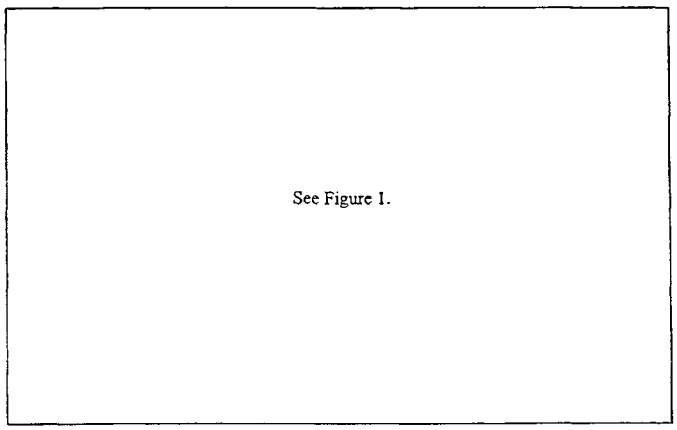

*Figure 2: Distributions of signal and nonsignal generated from the data set in Fig. 1.*

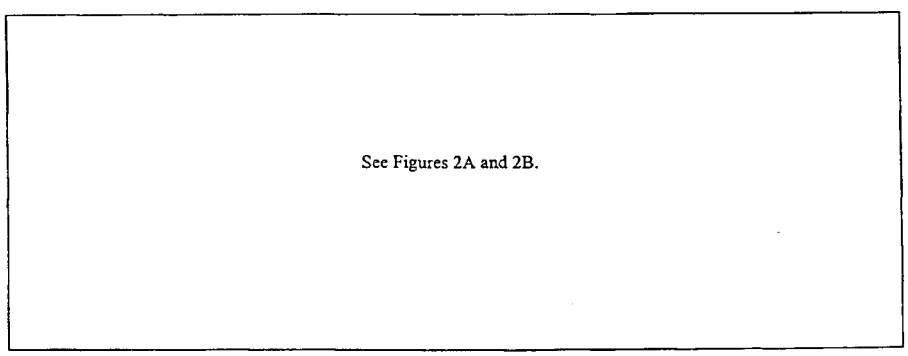

The Modeling Process

Step 1: Describe probability density functions for the two distributions, using modeling. We create a set of descriptors, that specify the nature of each distribution. To create these descriptors, we make an assumption that each distribution originates from a specific probability density function (pdf) which can be estimated from four parameters - mean, variance, proportion of the mixture, and class (e.g., Gaussian, gamma). A well-accepted method for deriving mean, variance, and proportion of mixture from mixed distributions is maximum likelihood estimation (MLE). Other methods could be used.

---

*Definitions*

Maximum likelihood method: We ask, "How likely is it that we would have obtained the actual data given values (generated by software or by the user) for four parameters for each distribution (mean, variance, proportion of mixture, and distribution class?" (e.g., Gaussian, gamma). The MLE procedure estimates the likelihood of obtaining the actual data given the initial values, and then proceeds to evaluate this likelihood given slightly different values. Iteration continues until it arrives at a likelihood that is at its maximum or until a predefined iteration limit is reached.

Probability density function: A curve (e.g., Gaussian) defined by a mathematical equation. Probabilities for ranges of values (e.g., $x > 100$; $x < 500$) can be derived based on area under the curve.

---

The MLE procedure generates pdfs for the signal and nonsignal distributions (Figure 3). These distributions include areas that are unambiguously part of one distribution or another. They also contain an area of overlap, and it is in this overlap area that our process operates to assign the origin of data points.

*Figure 3: Probability density functions of the signal and nonsignal distributions, showing the region of overlap. Within this region, our process assigns hybridization values to distribution of origin.*

See Figure 3.

Step 2: Use the probability density function to assign hybridization values to their distribution of origin. For any hybridization value, we can determine the probability of obtaining a value that large or larger from the nonsignal distribution or that small or smaller from the signal distribution. In this way, we obtain two probabilities (one that the value came from the nonsignal distribution and one that the value came from the signal distribution). Comparing the two probabilities tells us which distribution is the more likely originator of the data value.

Consider the values reported in Table 1, which were taken from the simulated data discussed in Appendix A. There are three things to note:

1. Higher values are less likely to have come from the nonsignal distribution (see Column 2) and more likely to have come from the signal distribution (see Column 3).
2. The probabilities in Columns 2 and 3 show which of the two distributions is more likely to be the origin of a particular hybridization value. For example, the probability that a value of 40 or greater came from the nonsignal distribution is .2107. The probability that a value of 40 or lesser came from the signal distribution is .0995. Our procedure establishes that a value of 40 is more likely to have come from the nonsignal distribution.
3. A criterion value for signal and nonsignal hybridization can be obtained from the probability function. In our example, a value less than or equal to 49 is categorized as nonsignal and greater than 49 is categorized as signal.

Table 1. Probabilities of origin for various hybridization values.

| Value | Probability of Originating from the Nonsignal Distribution | Probability of Originating from the Signal Distribution | More Likely Originating Distribution |
|---|---|---|---|
| 40 | .2107 | .0995 | Nonsignal |
| 45 | .1740 | .1258 | Nonsignal |
| 49 | .1493 | .1482 | Nonsignal |
| 50 | .1436 | .1540 | Signal |
| 60 | .0980 | .2148 | Signal |
| 70 | .0669 | .2788 | Signal |
| 78 | .0493 | .3308 | Signal |

Step 3: Test Goodness of Fit. The present invention creates models which purport to describe real data. We can evaluate the models using a goodness of fit parameter based on the chi-square statistic. The test can be automated, and the software flags cases in which the modeling results in a bad fit.

When Modeling is Appropriate

The modeling procedure assumes that the array of hybridization data points can be parsed into multiple distributions, each with sufficient members to allow accurate modeling. This is usually the case with nylon arrays, which contain large nonsignal components (Figure 4). Many glass arrays are quite different in nature. The background tends to be much lower, and the signal to noise higher. Therefore, it may not be possible or necessary to model a nonsignal distribution for very clean arrays. In the case of a clean glass array with a single label, we can assume a single (signal) distribution, dispense with the modeling, and use a simple signal criterion to discriminate usable assays (e.g. assays with a signal to noise ratio >3:1).

*Figure 4: Distributions of data showing two nonsignal proportions. Top is a 32P-labeled Clonetech Atlas array on nylon. There is a large nonsignal component. Bottom is a Cy3-labeled glass microarray (muscle tissue). The nonsignal component is very small.*

See Figures 4A and 4B.

Modeling a Real Specimen

To summarize the situation to this point:

We have demonstrated that modeling works well with a theoretical distribution.
We have shown that membrane arrays have the properties of the theoretical distribution.
Clean glass microarrays may not have enough nonsignal points to allow modeling.

Will the modeling be useful with glass? To answer this question, we examined some microarrays that are less clean than our excellent lymphocyte library array. In fact, these arrays have many of the properties of membranes (Figs. 5,6). Therefore, the modeling will be useful with a broad variety of arrays, including fluorescent microarrays.

*Figure 5:* A Cy3 fluorescent microarray image integrating three replicates of a spinal cord library. The dim red dots represent nonsignal. The brighter red dots fall into the area of overlap where the modeling might assign them to either signal or nonsignal. Other colors are unambiguously signal.

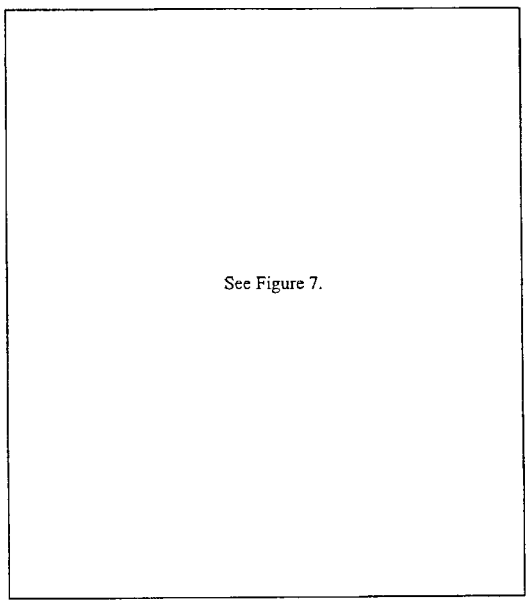

*Figure 6:* Modeling of the array in figure 5. The red lines show the distributions of signal and nonsignal. The blue shows intensity bins. The green line represents the modeled fit to the actual data. The model does not differ, significantly, from the data ($\chi 2$ test).

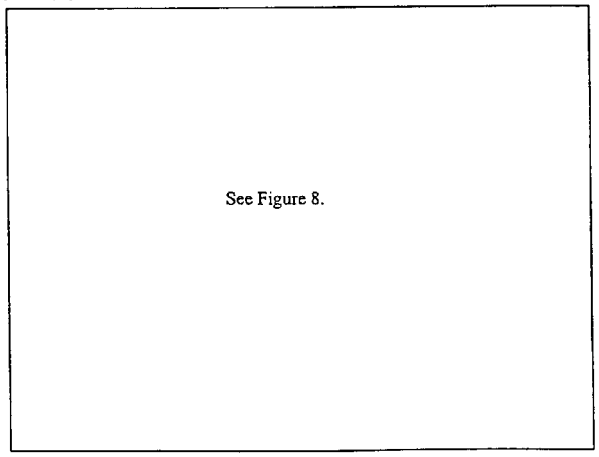

Summary of Distribution Modeling

We use modeling procedures to deconvolve a data matrix into two or more probability density functions. Hybridization data are then assigned to the most likely distribution of origin. Advantages of the modeling are:

- no need to create reference arrays to estimate nonsignal;
- objective assignment of hybridization values to signal or nonsignal distributions, to one label or another, or to any other deconvolved distributions.

The process can include a goodness of fit test, which alerts us if the outcome of the modeling is suspect.

*Reliability and Confidence Intervals*

Any hybridization assay is an estimate. That is, if we repeat the assay a number of times, we will obtain values which vary about a mean. All of these observed values estimate a true hybridization value. Some assay values are reliable estimates of the true value, and others are not. It is useful to specify the extent to which any given expression value is reliable.

Confidence intervals bracket a true value. In defining confidence limits for hybridization, we use the observed values as estimates, and generate ranges around the estimates. Given an observed value of X, and an estimate of the reliability of the observed value, we can give a range within which the true hybridization value estimated by X should lie. This range is stated with a particular confidence (e.g., > 95%).

We can also use the range data to specify our confidence in differences between assay values or expression ratios. If the ranges overlap, we have low confidence in the differences. If the ranges do not overlap, we have high confidence.

The Process: Replicates Are Present

If replicates are present, measurement error can be determined, directly. The additional advantage of replicates is that error associated with an average is decreased by a factor of $1/\sqrt{n}$ where $n$ is the number of replicates.

Step 1: Identify highly unreliable assays using estimates of variance derived from the replicates. Estimates of variability across replicates will vary from assay to assay. If they vary too much, the assay should be discarded. How do we set the criterion for discarding an assay?

We examine the variability of the variability. From this, we can identify replicates whose variability exceeds a value. The value is determined by calculating the variance of the variance values, and setting an objective variance criterion (e.g. 3 SD units) to indicate outliers.

Step 2: Determine error estimates for the acceptable assays using either standard error of the mean or coefficient of variation. True assay values are estimated by the mean of the replicates. The process can use either the standard error of the mean ($\hat{\sigma}_{\bar{x}}$, eq 1) or the coefficient of variation for the mean ($CV_{\bar{x}}$, eq. 2) to estimate assay error from the replicates.

Statistical Informatics

Equation 1. Standard error of the mean of the replicates for a given assay.

$$\hat{\sigma}_{\bar{x}} = \hat{\sigma}_x / \sqrt{N},$$
where $\hat{\sigma}_x$ = the standard deviation of the replicates, and $N$ = the number of replicates.

Equation 2. Coefficient of variation for the mean of the replicates for a given assay.

$$\text{Percentage CV}_{\bar{x}} = 100(\hat{\sigma}_{\bar{x}}/\bar{x}).$$

In the case of additive error (e.g., 100 ± 10, 1000 ± 10), the standard deviation is the best estimator of variance around each data point. The absolute value of error remains constant.

In the case of proportional error (e.g., 100 ± 10, 1000 ± 100), the coefficient of variation is a more useful measure of variability. The standard deviation changes proportionally to the magnitude of the measurement value.

Raw score hybridization assays will, typically, present proportional error, whereas log transformed assays will present additive error. The appropriate statistic is chosen on that basis.

To summarize the process, we obtain an average SD or CV for the replicates in the entire array. We then use that average in the next step.

Step 3: Calculation of confidence intervals. Error estimates for the assays allow us to construct confidence intervals around each assay. The higher the confidence we wish to have, the broader the range that brackets the true value. The range of possible values at a particular *confidence level* is called a "*confidence interval*." Ninety-five percent and 99% confidence are typical confidence levels.

Confidence level: The probability that our range includes the true value.
Confidence interval: The actual values of the range.

Step 4. Using confidence intervals for comparisons among assays. The measured values for any two assays will almost certainly differ from each other. These differences may simply reflect the effects of measurement error or they may reflect actual differences between the true values. We use confidence intervals to give probabilities that an observed difference is real.

If the confidence intervals of two assays do not overlap, we have confidence at the chosen level (e.g., 95 or 99%), that the true values of the assays differ from each other. If the confidence intervals overlap, we do not have confidence that the true values differ.

The advantages of our procedures are:

- Error is calculated from replicates, using standard statistical procedures.
- The confidence intervals are calculated directly from the array data.
- Confidence intervals are stated, using objective criteria.
- Expression comparisons are given with a probability of error.

RECTIFIED SHEET (RULE 91)
ISA/EP

The Process: Replicates Are Not Present

If replicates are not present, statistically derived estimates of reliability are unavailable. However, we still need error estimates to construct confidence limits. These error estimates are created in various ways. We can build some replicated assays into the array, and estimate error from these (e.g. DeRisi et al., 1996). Alternatively, the user can enter some error value that is characteristic of his data sets.

Once an error estimate has been specified, confidence limits can be calculated and comparisons among expression values can be specified with probabilities.

Analyzing Differential Expression

Most modeling processes require large numbers of data points. Usually, comparing hybridization values across conditions does not provide large numbers of differentially expressed assays. Rather, there tends to be a large number of assays with similar ratios (usually 1:1), and a relatively few cases of differential expression (e.g. 4:1). This creates difficulties for accurate modeling.

Fortunately, we can take advantage of some properties of the ratio to conduct distributional modeling that do not require large numbers of data points.

The Process: Measurement Error Known

Generate confidence intervals for expression ratios using replicates or user entry to estimate measurement error. If we have estimates of the measurement errors associated with the numerator and denominator of a ratio, it is a simple matter to estimate the measurement error associated with the ratio.

*Equation 3. Percentage error for hybridization ratios (replicates present).*

$$\text{Percentage error A/B} = 100 \sqrt{\left(\frac{\hat{\sigma}_{\bar{x}_A}}{\bar{x}_A}\right)^2 + \left(\frac{\hat{\sigma}_{\bar{x}_B}}{\bar{x}_B}\right)^2}$$

where $(\hat{\sigma}_{\bar{x}_A}/\bar{x}_A)$ = the proportional error for each replicate mean in Array A.

Raw hybridization values are used in Equation 3. When measurement error is the same proportion from assay to assay within each array, Equation 3 produces the same percentage error for all A/B ratios.

An analogous procedure is used when there are no replicates but an estimate of measurement error is available (e.g., from reference values or prior studies; see Appendix A)

The Process: Measurement Error Unkown

Option 2. Generate confidence intervals for expression ratios using an estimate of measurement error derived from the distribution. Confidence intervals can be developed for ratios, using an estimate derived from the variability of non-differentially expressed values.

We examine the variability of the middle 50% of log transformed hybridization ratios, which are assumed to be approximately distributed according to a Gaussian distribution. An estimate of the variability of ratios that are not differentially expressed is derived from this measure. This estimate is then used as discussed in Step 2 to assign confidence limits to all ratios (Fig. 7).

*Figure 7: Confidence-based ratio evaluation. The assay at position 1,1 is compared to all other assays. Yellow indicates increased expression at 95% confidence ($p < .05$), and red at 99% confidence ($p < .01$).*

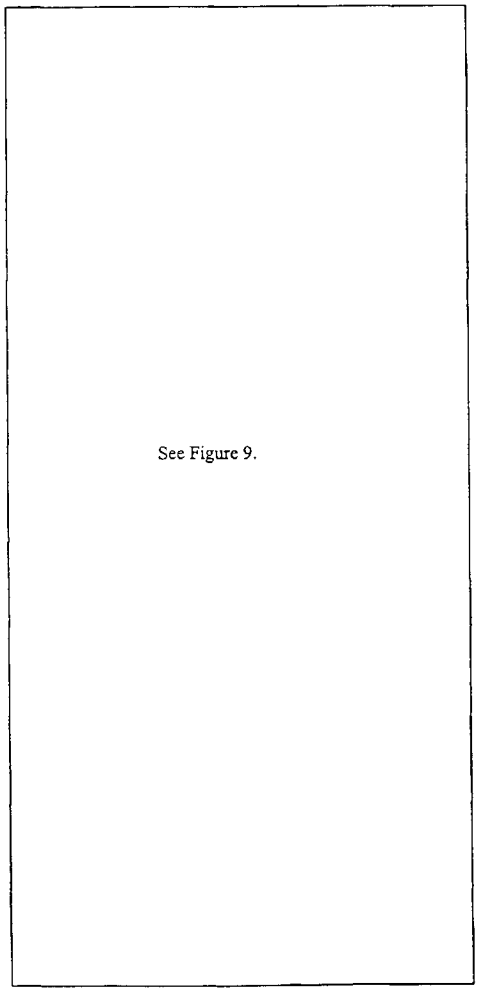

See Figure 9.

A Graphical Option

Model differential expression ratios using a Q-Q plot. The Q-Q plot is a member of the graphical statistics family. It maps frequency data to pdfs, in easily understood form. We use a Q-Q plot to model ratios of assays in one array divided by assays in another array (actually logs of the ratios of raw data). These ratios should present three partially overlapping distributions:

- values that do not differ across arrays (ratio 1:1);
- values that increase across arrays (ratio >1);
- values that decrease across arrays (ratio < 1);

The log values making up the distribution of values that do not differ should be normal. Therefore, we can use the central part of this distribution to model a complete distribution covering the range observed in the data. To the extent that observed values fail to lie within this distribution, they fall into the differentially expressed distributions (Figure 8).

*Figure 8. Q-Q plot comparing the distribution of differential expression ratios (red line) to the Gaussian distribution (green line). Where observed values lie in close proximity to the straight line describing the expected value, they fall into the distribution of values that do not differ across arrays. Where the observed values deviate from the expected values, they fall into the distributions of differential expression.*

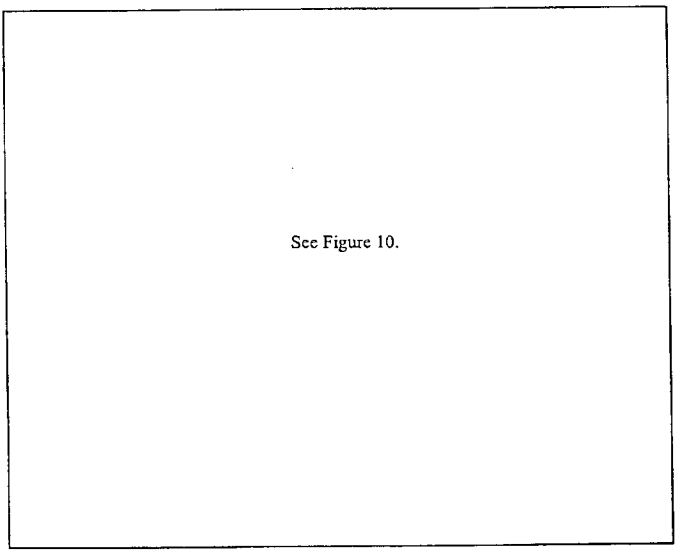

See Figure 10.

The advantage of this procedure is that it can be performed with any ratios, even if we have no direct estimate of measurement error.

RECTIFIED SHEET (RULE 91)
ISA/EP

References

DeRisi, J., Penland, L., Brown, P.O., Bittner, M.L., Meltzer, P.S., Ray, M., Chen, Y., Yan, A.S. and Trent, J.M. Use of a cDNA microarray to analyse gene expression patterns in human cancer, *Nature Genetics* 14:457-460 (1996).

de Saizieu, A., Certa, U., Warrington, J., Gray, C., Keck, W. and Mous, J. Bacterial transcript imaging by hybridization of total RNA to oligonucleotide arrays, *Nature Biotechnology* 16:45-48 (1998).

Nguyen, C., Rocha, D., Granjeaud, S., Baldit, M., Bernard, K., Naquet, P. and Jordan, B.R. Differential gene expression in the murine thymus assayed by quantitative hybridization of arrayed cDNA clones, *Genomics* 29:207-216 (1995).

Pietu, G., Alibert, O., Guichard, V., Lamy, B., Bois, F., Leroy, E., Mariage-Smason, R., Houlgatte, R., Soulare, P. and Auffray, C. Novel gene transcripts preferentially expressed in human muscles revealed by quantitative hybridization of a high density cDNA array, *Genome Research* 6:492-503 (1996).

Schena, M., Shalon, D., Davis, R.W. and Brown, P.O. Quantitative monitoring of gene expression patterns with a complementary DNA microarray, *Science* 270:467-470 (1995).

Shalon, D., Smith, S.J. and brown, P.O. A DNA microarray system for analyzing complex DNA samples using two-color fluorescent probe hybridization, *Genome Research* 6:639-645 (1996).

What is claimed is:

1. A method for improving the reliability of physical measurements obtained from studies performed on an array of one of chemical and biological assays having a set of samples, each composed of a subset of replicates, comprising the step of estimating an error in measurement of a selected sample by deriving a statistical characteristic from errors obtained when measuring the set of samples, and utilizing the estimated error in measurement of the selected sample as a standard for accepting or rejecting the measurement of the selected sample.

2. The method of claim 1 wherein the statistical characteristic is used to estimate discrete instances of a measurement for the subset of replicate samples.

3. The method of claim 1 wherein the estimates of measurement error are used to plan, manage and control array hybridization studies on the basis of (a) the probability of detecting a true difference of specified magnitude between physical measurements of a given number of replicates, or (b) the number of replicates required to about a true difference of specified magnitude.

4. A method in which outlier measurements are identified using measurement error estimates arrived at as in claim 1, the outlier being a rejected measurement of the selected sample.

5. The method of claim 1, used to evaluate physical measurements obtained from biological and chemical assays conducted on at least on one of substrates, substrates containing wells, and test tubes, and combinations thereof.

6. The method of claim 3 used to evaluate physical measurements obtained from biological and chemical assays conducted in at least one of substrates, substrates containing wells, and test tubes, and combinations thereof.

7. The method of claim 4 used to evaluate physical measurements obtained from biological and chemical assays conducted in at least one of substrates, substrates containing wells, and test tubes, and combinations thereof.

8. The method of claim 2 wherein the estimates of measurement error are used to plan, manage and control array hybridization studies on the basis of (a) the probability of detecting a true difference of specified magnitude between physical measurements of a given number of replicates, or (b) the number of replicates required to detect a true difference of specified magnitude.

9. A method in which outlier measurements are identified using measurement error estimates arrived at as in claim 2, the outlier being a rejected measurement of the selected sample.

10. The method of claim 2, used to evaluate physical measurements obtained from biological and chemical assays conducted on at least one of substrates, substrates containing wells, and test tubes, and combinations thereof.

* * * * *